United States Patent [19]

Cousse

[11] 3,987,175

[45] Oct. 19, 1976

[54] DERIVATIVES OF PHENOXY ISOBUTYRIC ACID HAVING HYPOLIPEMIZING AND HYPOCHOLESTEROLEMIZING ACTION

[75] Inventor: Henri Cousse, Castres (Tarn), France

[73] Assignee: Pierre Fabre S.A., Paris, France

[22] Filed: May 14, 1975

[21] Appl. No.: 577,402

[30] Foreign Application Priority Data
May 15, 1974 France .................. 74.16962

[52] U.S. Cl. .................. 424/266; 260/295.5 A
[51] Int. Cl.² .............. C07D 213/56; A61K 31/455; C07D 213/90
[58] Field of Search ............... 260/295.5 A; 424/266

[56] References Cited
UNITED STATES PATENTS

| | | | |
|---|---|---|---|
| 3,622,587 | 11/1971 | Carlson et al. | 260/295.5 R |
| 3,723,446 | 3/1973 | Scherm et al. | 260/295.5 R |
| 3,770,753 | 11/1973 | Beaufour | 260/295.5 A |

*Primary Examiner*—Alan L. Rotman
*Attorney, Agent, or Firm*—Gordon W. Hueschen

[57] ABSTRACT

The present invention relates to new chemical products which are useful as hypolipemizing and hypocholesterolemizing agents.

The new compounds are derivatives of phenoxy isobutyric acid of the general formula

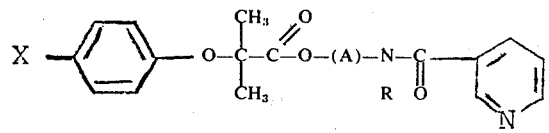

wherein:

A is a lower-alkylene bridge of 2 to 6 carbon atoms, either linear or branched,

X is a halogen atom,

R = H or lower-alkyl,

The N of the pyridyl ring can be replaced by an N-oxide, or the compounds can be in the form of their pharmaceutically-acceptable acid addition salts.

Pharmaceutical compositions containing these active principles are useful for hypolipemizing and hypocholesterolemizing purposes, e.g., in the prevention and treatment of atherosclerosis and its consequences.

9 Claims, No Drawings

DERIVATIVES OF PHENOXY ISOBUTYRIC ACID HAVING HYPOLIPEMIZING AND HYPOCHOLESTEROLEMIZING ACTION

The present invention concerns new derivatives of phenoxy isobutyric acid which can be used in therapy. In particular, they are useful as drugs having a hypolipemizing and hypocholesterolemizing action.

The invention also relates to pharmaceutical compositions containing these new compounds, and to methods of using them for their hypolipemizing and hypocholesterolemizing actions.

It is admitted that there is a relationship between the risk of arteriothrombosis and most disturbances of lipidic metabolism. In order to correct these disturbances, drugs containing clofibrate or nicotinic acid are customarily used. However, these two active principles do not act precisely on the same factors and a combining of them is frequently necessary for an adequate treatment of the disturbances observed. The chemical compounds which form the object of the present invention overcome this drawback by providing a more complete treatment since they have a broader spectrum of action.

The new chemical compounds have the general formula

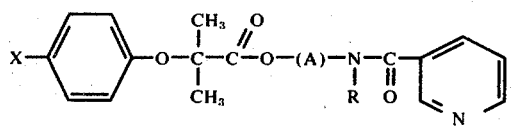

wherein:

A is a lower-alkylene bridge of 2 to 6 carbon atoms, either linear or branched,

X is a halogen atom,

R = H or lower-alkyl,

The N of the pyridyl ring can be replaced by an N-oxide. Their therapeutically-acceptable salts with inorganic or organic acids also form part of the invention.

As acids suitable for the formation of acid addition salts according to conventional procedure, there may be mentioned from the mineral series the following acids: hydrochloric, hydrobromic, methanesulfonic, isothionic, sulfuric, phosphoric, and sulfamic acids, and from the organic series: acetic, propionic, maleic, fumaric, tartaric, citric, oxalic, and benzoic acids, to name a few.

The new compounds can be obtained in particular in accordance with the following manner of synthesis:

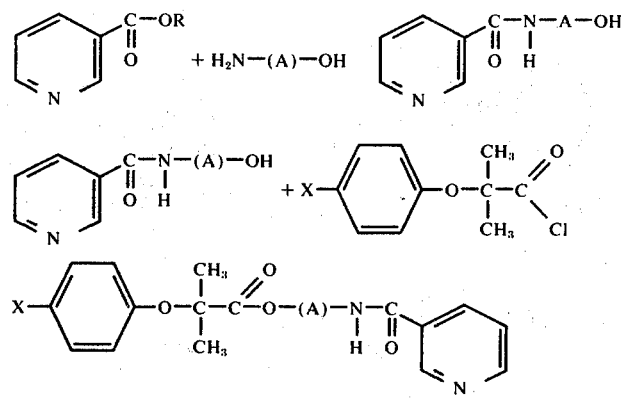

The same series of reactions exactly is followed for the production of a compound of the invention wherein R is lower-alkyl, with the sole change that one starts with an amino alkanol wherein one of the hydrogen atoms of the primary amine group as shown in the foregoing reaction scheme is replaced by a lower-alkyl group, thereby producing a compound wherein the hydrogen attached to the nitrogen atom in the final product is replaced by an R radical, wherein R is lower-alkyl. Such lower-alkyl substituted aminoalkanols are well known in the art.

One method of obtaining a derivative of the series is described below in detail, it being pointed out that this method can be generalized to all compounds of the chemical family. The following Examples illustrate the invention, but are not to be construed as limiting.

EXAMPLE 1

Hydrochloride of N-nicotinoyl, O-(p-chloro phenoxy) isobutanoyl ethanol amine: (F 1393)

a. Obtaining of the N-(hydroxy-2 ethyl)nicotinamide

Introduce in succession 1 mole of ethyl nicotinate and 1 mole of ethanolamine into a round bottom flask.

Heat the mixture on an oil bath at about 150° C. for 4 hours with agitation.

The ethanol is distilled off as it is formed; when the theoretical amount of ethanol has been recovered, the reaction is complete.

The amide obtained crystallizes out; the mass may be recrystallized from chloroform.

The yield is quantitative, from 90 to 100% depending on the individual case.

This derivative has a melting point of 92° C.; in the infrared it has the characteristic absorption bands and in particular $\nu$ C = O (amide) at 1655 cm$^{-1}$.

b. Synthesis of the hydrochloride of N-(ethyl-2-p-chlorophenoxy isobutyrate) nicotinamide To a solution formed of 1 mole of N-hydroxy ethyl nicotinamide in 500 ml of chloroform, add with agitation a solution of 1 mole of (p-chlorophenoxy)isobutyroyl chloride in 500 ml of chloroform.

Heat under reflux for 6 hours; upon cooling, the expected product precipitates.

The crystals are filtered, centrifuged, and then washed with a small amount of chloroform.

The yield is 86% of product recrystallized from boiling ethanol.

This derivative has the formula

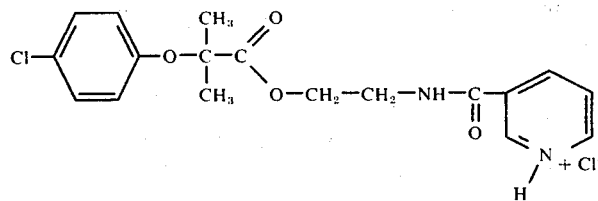

This product may also be referred to as the hydrochloride of N-(ethyl-2-p-chlorophenoxy isobutyrate)-nicotinamide.
Empirical formula: $C_{18}H_{20}Cl_2N_2O_4$
Molecular weight: 399.3
  White crystals
  Instantaneous melting point: 150°
  Slow melting point: 130°
Plate chromatography:
  support: Merck silica F 254
  solvent: acetic acid/dioxane/benzene 4/25/90
  development: under ulraviolet lamp
  Rf: 0.5
Solubility characteristics:
  12% soluble in water, 3.5% in ethanol, 5% in propylene glycol, and 16% in N-methyl pyrrolidone.

Other pharmaceutically-acceptable acid addition salts are prepared, if desired, by neutralizing the hydrochloride and reacidifying with a selected mineral or organic acid, as already explained in the foregoing and as is conventional in the art.

EXAMPLE 2

Characteristics of another chemical compound obtained by the process described above.

N-oxide of N-nicotinoyl, O-(parachloro phenoxy) isobutanoyl ethanol amine (F 1416)

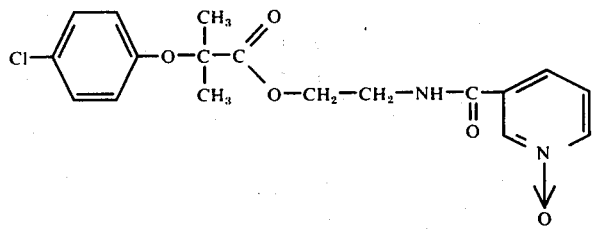

This compound may also be referred to as the N-oxide of N-(ethyl-2-p-chlorophenoxy isobutyrate)-nicotinamide.
Formula: $C_{18}H_{19}ClN_2O_5$
Molecular weight: 378.8
  White needles
  Melting point: 130° C.
Plate chromatography:
  support: silica
  solvent: butanol/acetic acid/water 6/2/2
  development: ultraviolet lamp and iodine vapor
  Rf: 0.72
  Insoluble in water, 1% soluble in propylene alcohol, 3% in ethanol.

EXAMPLE 3

Other compounds.

In the same manner as given in Example 1, the corresponding hydrobromide of N-nicotinoyl, O-(para-bromo phenoxy) isobutanoyl ethanol amine is prepared from the appropriate starting materials wherein the chlorine atoms in the starting material are substituted by bromine atoms.

In exactly the same manner, the process of Example 1 is repeated but starting instead with the (p-fluoro phenoxy)isobutyroyl chloride with production of the hydrochloride of N-nicotinoyl, O-(para-fluoro phenoxy) isobutanoyl ethanol amine.

Similarly, the process of Example 1 is repeated, but using, in step (a) of Example 1, 2-amino propanol instead of ethanol amine. The resulting product is the hydrochloride of N-nicotinoyl, O-(para-chloro phenoxy) isobutanoyl isopropanol amine.

In like manner, following the procedure of Example 1, but using, in step (a), methyl amino ethanol instead of the ethanol amine employed therein, the compound N-nicotinoyl, O-(para-chloro phenoxy) isobutanoyl ethanol methylamine, wherein R in the general formula is the methyl group, is obtained. In exactly the same manner, the corresponding compounds wherein R is ethyl, propyl, isopropyl, butyl, isobutyl, amyl, hexyl, heptyl, and octyl, are produced, starting only from the appropriately R-substituted ethanol amine or, where a different A group is produced, an appropriately substituted lower-alkanol amine, such as propanol amine, butanol amine, hexanol amine, or the like.

In the same manner, by carrying out the procedure of Example 1, with obvious variations as taught by the general disclosure hereof, various other compounds within the scope of the invention and pharmaceutically-acceptable acid addition salts or N-oxides thereof are produced.

Pharmacology

The pharmacological experiments made it possible to note remarkable hypolipemizing and hypocholesterolemizing properties. The verification was effected in several tests proving the broad spectrum of activity of the molecules in question.

The above-described chemical compounds were submitted to toxicity tests. The acute toxicity of certain compounds determined by the 50% lethal dose is entered in the following Table:

| Compound | Manner of Administration | $LD_{50}$ in mg/kg |
|---|---|---|
| F 1393 | by mouth | 3100 |
|  | ip | 560 |
| F 1416 | by mouth | 2400 |
|  | ip | ≥ 1000 |

The $LD_{50}$ was studied in accordance with the method of Miller and Tainter, the mortality of mice being observed for 4 days.

There are reported below more particularly the results obtained with the compound F 1393, which has been systematically compared with the reference products, clofibrate and nicotinic acid.

1. Acute test

The products to be studied were administered intraperitoneally to groups of identical rats; the doses were calculated on a basis of clofibrate in order to make the tests fully comparative. After a period of 4 hours, blood was removed by heart puncture and cholesterol and triglycerides determined. The results are set forth in the following Table:

| Product | Dose mg/kg | No. of animals | Cholesterol % variation referred to the control | Triglycerides % variation referred to the control |
|---|---|---|---|---|
| Clofibrate | 200 | 10 | −17 | +23 |
| Nicotinic acid | 140 | 10 | −25 | −47 |
| F 1393 | 340 | 10 | −32 | −43 |

The activity of F 1393 being thus shown, F 1393 in smaller doses was thereupon studied:

| Doses of F 1393 | Cholesterol % variation referred to the control | Triglycerides % variation referred to the control |
|---|---|---|
| 50 mg/kg | −10 NS | −26 HS |
| 100 mg/kg | −0 | −29 HS |
| 200 mg/kg | −22 HS | −19 S |
| 340 mg/kg | −35 HS | −43 HS |

(NS = not significant; HS = highly significant).

It is noted that the activity on the triglycerides is retained for low doses of 50 mg/kg.

2. Test covering 4 days of treatment by oral administration. In a lot of 30 rats subjected to a normal diet, the blood samplings were effected and the determinations of cholesterol and lipoproteins (Kunkel's phenol test) were made on the fifth day.

| Product | Dose mg/kg | Cholesterol % variation referred to the control | Kunkel phenol test % variation referred to the control |
|---|---|---|---|
| Clofibrate | 200 | −34 | −29 |
| Nicontinic acid | 100 | −22 | + 6 |
| F 1393 | 340 | −44 | −52 |

3. Hypocholesterolemia induced by the administration of Triton WR 1339

Groups of male rats were used from whom a sample of the blood is taken for the control determinations and on which an IV injection of Triton is effected in a dose of 200 mg/kg.

Immediately after the injection, the products to be tested were administered IP and new samples of blood taken 18 hours later (at the maximum of the hypocholesterolemia produced by the Triton).

Manner of calculation:
P being the biochemical parameter under consideration $$\left[1 - \frac{\dfrac{p\ \text{Triton + product}}{+ 18\ \text{hours}} - \dfrac{p\ \text{Triton + product}}{\text{at the start}}}{\dfrac{p\ \text{Triton}}{+ 18\ \text{hours}} - \dfrac{p\ \text{Triton}}{\text{at the start}}}\right] \times 100$$

| Product | Dose mg/kg | Cholesterol % variation | Kunkel phenol % variation |
|---|---|---|---|
| Clofibrate | 200 | −15 NS | −23 NS |
| Nicotinic acid | 100 | −67 HS | −75 HS |
| F 1393 | 340 | −68 HS | −89 S |

There is thus observed an effect parallel to that of nicotinic acid, while the clofibrate is inactive in this test.

4. Testing of the rats subjected to a fatty diet creating hyperlipidemias:

The animals are subjected for 15 days to a diet supplemented by
5% cholesterol
40% butter
2.5% bile salts Parallel with this the treated animals receive the products to be tested orally; on the 15th day in the evening all food is removed from the animals and on the 16th day the blood samples are taken by cardiac puncture.

A complete lipidic balance is established at the start and at the end of the experiment.

The animals are distributed in 5 lots of 10 male rats each:
1 lot absolute control
1 lot fatty-diet control
1 lot fatty-diet + F 1393 at 340 mg/kg
1 lot fatty-diet + clofibrate at 200 mg/kg
1 lot fatty-diet + nicotinic acid at 100 mg/kg a. The method is validated by the study of the variation of the fatty diet controls as compared with the absolute controls; the percentage variation is evaluated by the formula:

$$\frac{P\ \text{control}\ RG - P\ \text{absolute control}}{P\ \text{absolute control}} \times 100$$

The results are as follows:

| Parameter | % variation |
|---|---|
| total lipids | +227.8 |
| total cholesterol | +472.9 |
| triglycerides | −14.8 (NS) |
| Kunkel phenol test | +927.2 |
| Burnstein test (β lipoproteins) | +2296 |

It will therefore be noted that the fatty diet very substantially increases all the parameters with the exception of the triglycerides, the percentage of which has not changed.

b. Study of the influence of the different products on the modifications of the lipid balance induced by the fatty diet.

The % of action of a product is calculated in accord with the formula $$\frac{P \text{ control fatty diet} - P \text{ (control fatty diet + product)}}{P \text{ control fatty diet} - P \text{ control absolute}} \times 100$$

| Product | F 1393 | Clofibrate | Nicotinic Acid |
|---|---|---|---|
| Total lipids | ↘47.3 | ↘20.9 | ↘10.6 |
| Total cholesterol | ↘58.2 | ↘18 | ↘26 |
| Kunkel phenol test | ↘65.2 | ↘35.6 | ↘56.9 |
| Burnstein test | ↘59.7 | ↘19.6 | ↘28.3 | c. Special case of the triglycerides

As the triglycerides are not increased by the fatty diet, a different method of calculation was adopted:

A. action of the product compared with the absolute control lot $$\% \text{ of action} = \frac{\text{triglycerides absolute control} - \text{triglycerides product}}{\text{triglycerides absolute control}} \times 100$$

| Product | % variation |
|---|---|
| F 1393 | ↘54.3 |
| Clofibrate | ↘32 |
| Nicotinic acid | ↘20.9 |

B. action of the product as compared with the fatty acid control lot:

$$\% \text{ of action} = \frac{\text{triglycerides (fatty diet control)} - \text{triglycerides (fatty diet + product)}}{\text{triglycerides (fatty diet control)}} \times 100$$

| Product | % variation |
|---|---|
| F 1393 | ↘46.3 |
| Clofibrate | ↘20.2 |
| Nicotinic acid | ↘7.2 |

Moreover, the pharmacological tests made it possible to show vasodilatory properties which have the advantage of not appearing abruptly.

Therapeutic application

The very conclusive results obtained in pharmacology on the compound F 1393 led to carrying out a chronic toxicological study which was to precede the clinical tests reported below.

The clinical tests were directed at showing the therapeutic properties in the different types of hyperlipidemias, particularly in the prevention and treatment of atherosclerosis and its consequences.

Some subjects furthermore showed circulatory disturbances. The best results were obtained on:
essential hypocholesterolemias with hypolipoproteinemia,
the hypolipemias caused by carbohydrates and fats.

In most cases it is recommended to maintain an adequate food diet concomitantly with the treatment. As compared with the control drugs, more constant results were observed and in particular a prolonged effect after the stopping of the treatment, even if the diet was not followed strictly.

The results obtained with the pharmaceutical preparations containing the active principles forming the object of the invention are particularly interesting, since it is possible to apply intermittent treatments which are less difficult for the patient and without a hypocholesterolemia or hyperlipemia rebound effect occurring.

The clinical experiments were carried out preferably on a double-blind basis, namely, with the chofibrate or with the nicotinic acid, and in most of the cases treated the new medication proved superior.

The dosage required to obtain stabilization of the factors of lipidic metabolism may vary from one subject to the other. The treatments recommended include daily doses orally of 1 to 3 g/day in the form of repeated treatments. The tablets used for the experiment contained 500 mg of active principle.

The pharmacological properties, hereinabove described, of the compounds of the invention, enable their use in human and animal therapy, especially for the reduction of fats and the reduction of cholesterol in a living animal body, and the compounds of the invention may be administered in various different pharmaceutical forms, in conjunction or admixture with a pharmaceutically suitable solid or liquid carrier such, for example, as distilled water, lactose, talc, gum arabic, magnesium stearate, ethyl-cellulose, or the like. Although oral dosages are preferred, and amounts of 1 to 3 g/day in the form of repeated treatments are entirely suitable, broader ranges of 0.5 to 10 g/day may also be employed, depending upon the circumstances of the individual case. Although 500 mg. of active principle have been found especially suitable for use in tablets, the individual doses may vary from 200 to 1000 mg., and the dosages may of course be rectal or parenteral in addition to oral, in which case the size of the dose may generally be somewhat reduced, especially where parenteral administration is involved.

The compounds may be administered to a living animal body in any one of various ways, for example, orally as in capsules or tablets, parenterally in the form of sterile solutions, suspensions, or by pellet implantation, and in some cases intravenously in the form of sterile solutions. Other modes of administration are cutaneously, subcutaneously, bucally, intramuscularly, and intraperitoneally.

Pharmaceutical formulations of the active principles of the present invention are usually prepared from a predetermined quantity of one or more of the compounds of the invention, preferably in solid form. Such formulations may take the form of powders, elixirs, solutions, pills, capsules, pellets, or tablets, with or without but preferably with any one of a large variety of pharmaceutically-acceptable vehicles or carriers. When in admixture with a pharmaceutical vehicle or carrier, the active ingredient usually comprises from about 1 to about 75%, usually from about 2 to about 15%, by weight of the composition. Carriers such as starch, sugar, talc, commonly-used synthetic and natural gums, water, and the like, may be used in such formulations. Binders such as gelatin and lubricants such as sodium stearate may be used to form tablets. Disintegrating agents such as sodium bicarbonate may also be included in tablets if desired. The amount of active material employed will obviously vary greatly depending upon the body weight of the subject to which administered, and the particular result desired. The active agents of the invention may obviously be combined for administration with other pharmacologically-active agents. In such compositions, the proportion of the active agent or agents in the compositions may be varied widely. It is only necessary that the active ingredient of the invention constitute an effective amount, i.e., such that a suitable effective dose will be obtained consistent with the dosage form employed. Obviously, several dosage forms may be administered at or about the same time. The exact individual dosages as well as daily dosages in a particular case will of course be determined according to well-established medical and/or veterinary principles in accord with the directions of the physician or veterinarian in charge.

It is to be understood that the invention is not to be limited to the exact details of operation or exact compounds, compositions, or procedures shown and described, as obvious modifications and equivalents will be apparent to one skilled in the art.

I claim:

1. Phenoxy isobutyric acid amides selected from the group consisting of (a) a compound having the formula:

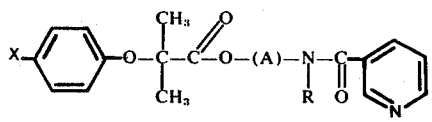

wherein:
A is a lower-alkylene bridge of 2 to 6 carbon atoms, inclusive,
X is a halogen atom selected from the group consisting of chlorine, fluorine, and bromine,
R is selected from the group consisting of hydrogen and lower-alkyl,
and (b) pharmaceutically-acceptable acid addition salts thereof, and (c) the N-oxide thereof.

2. The hydrochloride of N-(ethyl-2-p-chlorophenoxy isobutyrate)-nicotinamide.

3. The N-oxide of N-(ethyl-2-p-chlorophenoxy isobutyrate)-nicotinamide.

4. A pharmaceutical composition suitable for use for its hypolipemizing and hypocholesterolemizing action comprising a compound according to claim 1 in an effective hypolipemizing and hypocholesterolemizing amount together with a pharmaceutically-acceptable carrier therefor.

5. The pharmaceutical composition of claim 4, wherein the active ingredient is the hydrochloride of N-(ethyl-2-p-chlorophenoxy isobutyrate)-nicotinamide.

6. The pharmaceutical composition of claim 4, wherein the active ingredient is the N-oxide of N-(ethyl-2-p-chlorophenoxy isobutyrate)-nicotinamide.

7. The method of treating a living animal body having a tendency toward an excess of fat and cholesterol comprising the step of administering orally or parenterally to the said living animal body an effective hypolipemizing and hypocholesterolemizing amount of a compound of claim 1.

8. The method of claim 7 wherein the active hypolipemizing and hypocholesterolemizing compound is the hydrochloride of N-(ethyl-2-p-chlorophenoxy isobutyrate)-nicotinamide.

9. The method of claim 7 wherein the active hypolipemizing and hypocholesterolemizing compound is the N-oxide of N-(ethyl-2-p-chlorophenoxy isobutyrate)-nicotinamide.

* * * * *

UNITED STATES PATENT OFFICE
CERTIFICATE OF CORRECTION

Patent No. 3,987,175  Dated October 19, 1976

Inventor(s) Henri Cousse

It is certified that error appears in the above-identified patent and that said Letters Patent are hereby corrected as shown below:

Diagram in the abstract should read:

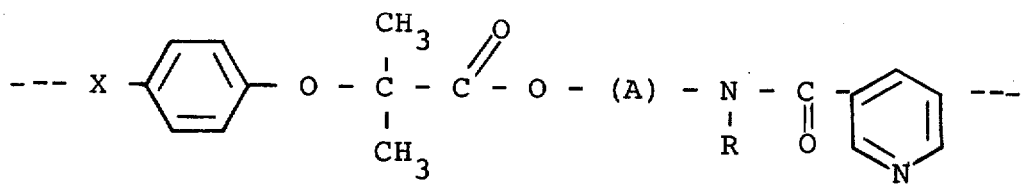

Column 3, first diagram should read:

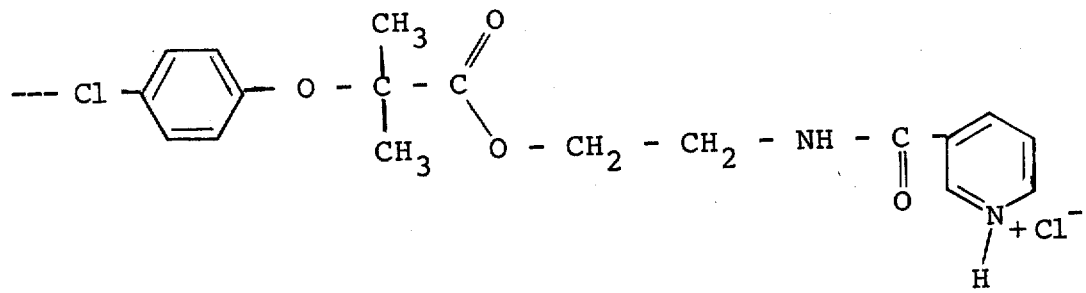

Column 8, line 11, "chofibrate" should read -- clofibrate --.

Signed and Sealed this

Fifteenth Day of February 1977

[SEAL]

Attest:

RUTH C. MASON
Attesting Officer

C. MARSHALL DANN
Commissioner of Patents and Trademarks